US011285461B2

(12) United States Patent
Jantharasuk et al.

(10) Patent No.: US 11,285,461 B2
(45) Date of Patent: Mar. 29, 2022

(54) CATALYST SYSTEM AND PROCESS UTILIZING THE CATALYST SYSTEM

(71) Applicant: SMH Co., Ltd, Bangkok (TH)

(72) Inventors: Amnart Jantharasuk, Rayong (TH); Kongkiat Suriye, Samut-Prakan (TH)

(73) Assignee: SMH Co., Ltd, Bangkok (TH)

( * ) Notice: Subject to any disclaimer, the term of this patent is extended or adjusted under 35 U.S.C. 154(b) by 56 days.

(21) Appl. No.: 16/468,906

(22) PCT Filed: Nov. 16, 2017

(86) PCT No.: PCT/EP2017/079501
§ 371 (c)(1),
(2) Date: Jun. 12, 2019

(87) PCT Pub. No.: WO2018/108443
PCT Pub. Date: Jun. 21, 2018

(65) Prior Publication Data
US 2019/0314788 A1   Oct. 17, 2019

(30) Foreign Application Priority Data

Dec. 13, 2016 (EP) ..................................... 16203704

(51) Int. Cl.
| | |
|---|---|
| *B01J 21/04* | (2006.01) |
| *B01J 21/06* | (2006.01) |
| *B01J 21/08* | (2006.01) |
| *B01J 21/10* | (2006.01) |
| *B01J 21/12* | (2006.01) |
| *B01J 23/02* | (2006.01) |
| *B01J 23/26* | (2006.01) |
| *B01J 23/28* | (2006.01) |
| *B01J 23/30* | (2006.01) |
| *B01J 23/36* | (2006.01) |
| *B01J 23/40* | (2006.01) |
| *B01J 23/42* | (2006.01) |
| *B01J 23/44* | (2006.01) |
| *B01J 23/46* | (2006.01) |
| *B01J 35/00* | (2006.01) |
| *B01J 29/40* | (2006.01) |
| *B01J 29/16* | (2006.01) |
| *B01J 29/70* | (2006.01) |
| *C10G 11/04* | (2006.01) |
| *C10G 65/10* | (2006.01) |
| *B01J 29/076* | (2006.01) |

(52) U.S. Cl.
CPC .............. *B01J 23/02* (2013.01); *B01J 21/04* (2013.01); *B01J 21/10* (2013.01); *B01J 35/0006* (2013.01); *C10G 11/04* (2013.01); *C10G 65/10* (2013.01); *B01J 21/066* (2013.01); *B01J 21/08* (2013.01); *B01J 29/076* (2013.01); *B01J 2523/13* (2013.01); *B01J 2523/22* (2013.01); *B01J 2523/23* (2013.01); *B01J 2523/31* (2013.01); *B01J 2523/33* (2013.01); *B01J 2523/36* (2013.01); *B01J 2523/3706* (2013.01); *B01J 2523/3787* (2013.01); *B01J 2523/43* (2013.01); *B01J 2523/67* (2013.01); *B01J 2523/68* (2013.01); *B01J 2523/69* (2013.01); *B01J 2523/74* (2013.01); *B01J 2523/824* (2013.01); *B01J 2523/827* (2013.01); *B01J 2523/828* (2013.01)

(58) Field of Classification Search
CPC . B01J 21/04; B01J 21/06; B01J 21/063; B01J 21/066; B01J 21/08; B01J 21/12; B01J 23/26; B01J 23/28; B01J 23/30; B01J 23/36; B01J 23/40; B01J 23/42; B01J 23/44; B01J 23/468; B01J 29/40; B01J 29/163; B01J 29/166; B01J 29/7007; B01J 35/0006; B01J 21/10; B01J 23/02; C10G 11/04; C10G 65/10
See application file for complete search history.

(56) References Cited

U.S. PATENT DOCUMENTS

| | | | |
|---|---|---|---|
| 5,243,120 A | 9/1993 | Slaugh | |
| 5,905,051 A | 5/1999 | Wu et al. | |
| 9,034,286 B2 * | 5/2015 | Bergeal ................. | B01D 53/945 |
| | | | 423/213.5 |
| 9,057,310 B2 * | 6/2015 | Bergeal ................. | B01D 53/922 |
| 9,527,034 B2 * | 12/2016 | Bergeal ................. | B01J 37/0215 |
| 9,527,035 B2 * | 12/2016 | Bergeal ................. | B01J 37/0215 |
| 10,279,314 B2 * | 5/2019 | Bergeal ................. | B01D 53/944 |
| 2004/0152586 A1 * | 8/2004 | Ou ........................ | B01J 23/002 |
| | | | 502/64 |

(Continued)

FOREIGN PATENT DOCUMENTS

EP   3069788 A1   9/2016

OTHER PUBLICATIONS

Jan. 25, 2018, International Search Report and Written Opinion, PCT/EP2017/079501.

*Primary Examiner* — Cam N. Nguyen

(74) *Attorney, Agent, or Firm* — Banner & Witcoff, Ltd.

(57) ABSTRACT

This invention relates to a catalyst system comprising (a) at least one layer of a first catalyst comprising a dehydrogenation active metal on a solid support; (b) at least one layer of a second catalyst comprising a metal oxide; and (c) at least one layer of a third catalyst comprising a transition metal on an inorganic support; wherein the at least one layer of a second catalyst is sandwiched between the at least one layer of a first catalyst and the at least one layer of a third catalyst; and a process comprising contacting a hydrocarbon feed with the catalyst system.

19 Claims, No Drawings

(56) References Cited

U.S. PATENT DOCUMENTS

2007/0106089 A1\* 5/2007 Benderly ................ C07C 57/04
560/211
2008/0194400 A1\* 8/2008 Schmidt ............... B01J 37/0244
502/223
2010/0274063 A1\* 10/2010 Wang ..................... C10G 11/05
585/324

\* cited by examiner

CATALYST SYSTEM AND PROCESS UTILIZING THE CATALYST SYSTEM

CROSS-REFERENCE TO RELATED APPLICATIONS

This application is a U.S. National Stage application under 35 U.S.C. § 371 of International Application PCT/EP2017/079501 (published as WO 2018/108443 A1), filed Nov. 16, 2017, which claims the benefit of priority to Application EP 16203704.8, filed Dec. 13, 2016. Benefit of the filing date of each of these prior applications is hereby claimed. Each of these prior applications is hereby incorporated by reference in its entirety.

The present invention relates to a catalyst system and a process for conversion of a hydrocarbon feed comprising a saturated hydrocarbon compound to olefin products utilizing the catalyst system.

Olefins, especially light olefins including ethylene and propylene, are valuable hydrocarbon products. They are useful for preparing a wide variety of end products, including ethylene oxide, propylene oxide, ethyl benzene, acetone, phenol, polyethylene, polypropylene, other polymers, and other petrochemical products. Even though the prices have fluctuated over time, the demands in the industry have still been continuously growing.

To serve industrial needs, many methods have been used to produce olefins. However, it is typically more economically attractive to produce olefins from lower valued feedstock such as paraffins. A conventional method for converting saturated paraffins to olefins is thermal cracking. This is a highly energy intensive method and product selectivity is difficult to be adjusted and controlled.

Catalytic cracking is a later developed method. With appropriate catalytic materials, generally zeolite-based materials, hydrocarbon cracking can occur at less severe operating conditions.

In the art, also processes are known converting saturated paraffins to olefins by dehydrogenation utilizing an appropriate catalyst. The dehydrogenation process mainly converts saturated parraffin to an olefin with a corresponding number of carbon atoms. Integration between dehydrogenation and metathesis is also technically possible and is expected to finally provide different olefins product distribution which fulfills highest industrial needs.

When implementing a dehydrogenation-metathesis integrated process, numerous effects need to be optimized and controlled in order to achieve a desirable efficiency. For example, diverse side reactions may take place during dehydrogenation and metathesis, for example the (re)hydrogenation of the produced ethylene, propylene or butene which are otherwise preferred end products of the paraffin conversion process. Further, in the presence of hydrogen, hydrogenolysis and cracking of the paraffin feed materials, such as propane, may occur.

It is therefore an object of the present invention to provide a catalyst system for conversion of a hydrocarbon feed comprising a saturated hydrocarbon compound to olefin products and a respective process utilizing the catalyst system wherein high olefins selectivity is achieved with good conversion and stability of the catalyst system.

This object is achieved by a catalyst system comprising:
(a) at least one layer of a first catalyst comprising a dehydrogenation active metal on a solid support;
(b) at least one layer of a second catalyst comprising a metal oxide; and
(c) at least one layer of a third catalyst comprising a transition metal on an inorganic support;
wherein the at least one layer of a second catalyst is sandwiched between the at least one layer of a first catalyst and the at least one layer of a third catalyst.

With respect to the inventive catalyst system it may be provided that each of the first catalyst, the second catalyst and the third catalyst differs from both of the two other catalysts.

It may be provided that the solid support is different from the inorganic support.

It may be further provided that the dehydrogenation active metal is different from the transition metal. In a representative embodiment, the second composition does not comprise the dehydrogenation active metal, in particular the second composition does not comprise platinum, palladium, rhodium, chromium or mixtures thereof.

It is preferred that the metal oxide is present in the second catalyst in an amount of generally at least 90%, more typically at least 95%, by weight of the second catalyst.

In one embodiment, the at least one layer of a second catalyst consists of a metal oxide.

The metal oxide, in one embodiment, comprises, preferably consists of, magnesium oxide, calcium oxide, or a mixture thereof, more preferably magnesium oxide.

In one alternative embodiment, the metal oxide comprises, preferably consists of, a mixed magnesium-aluminium oxide, a mixed calcium-aluminium oxide, or a mix thereof, more preferably a mixed magnesium-aluminium oxide.

Preferably, the mixed magnesium-aluminium oxide and/or the mixed calcium-aluminium oxide in the second catalyst are derived from, more preferably by heat treatment of, a magnesium-aluminium layered double hydroxide or a calcium-aluminium layered double hydroxide respectively.

At least one of the compounds of the second catalyst, preferably all, may function as an adsorbent.

The catalyst system according to the invention is in one embodiment arranged so that the at least one layer of a first catalyst, the at least one layer of a second, and at least one layer of a third catalyst are stacked vertically. More preferably, the catalyst system is arranged so that a hydrocarbon feed stream is contacted with the at least one layer of a first catalyst first.

Amount of the at least one layer of a second catalyst in the catalyst system should be enough to prevent physical contact between the at least one layer of the first catalyst and the at least one layer of the third catalyst. This amount depends on factors including the of the at least one layer of a first catalyst, amount of the at least one layer of a third catalyst, and diameter of a reactor containing the catalyst system.

In one embodiment, the at least one layer of a first catalyst, the at least one layer of a second catalyst, and the at least one layer of a third catalyst are contained in the s e reactor, preferably a fixed-bed reactor.

In one embodiment, the catalyst system consists of:
(a) one layer of a first catalyst comprising a dehydrogenation active metal on a solid support;
(b) one layer of a second catalyst comprising a metal oxide; and
(c) one layer of a third catalyst comprising a transition metal on an inorganic support;
wherein the layer of a second catalyst is sandwiched between the layer of a first catalyst and the layer of a third catalyst.

In another embodiment, the catalyst system consists of:
(a) a first layer of a first catalyst comprising a dehydrogenation active metal on a solid support;
(b) a second layer of a second catalyst comprising a metal oxide;
(c) a third layer of a third catalyst comprising a transition metal on an inorganic support;
(d) a forth layer of a second catalyst comprising a metal oxide; and
(e) a fifth layer of a first catalyst comprising a dehydrogenation active metal on a solid support;
wherein the second layer of a second catalyst is sandwiched between the first layer of a first catalyst and the d layer of a third catalyst, and the forth layer of a second catalyst is sandwiched between the third layer of a third catalyst and the fifth layer of a first catalyst.

More layers may be contained in the catalyst system according to the present invention as long as a layer of a first catalyst comprising a dehydrogenation active metal on a solid support and a layer of a third catalyst comprising a transition metal on an inorganic support are always separated from each other by a layer of a second catalyst comprising a metal oxide.

In one embodiment, a weight ratio between the at least one layer of a first catalyst to the at least one layer of a third catalyst is in the range of 1:10 to 10:1, preferably 1:5 to 5:1, more preferably 1:3 to 3:1, even more preferably 1:2 to 2:1.

The dehydrogenation active metal refers to a group of metals that are efficient for dehydrogenation of a hydrocarbon. Dehydrogenation is a reaction in which hydrogen is detached from a molecule. In one embodiment, the dehydrogenation active metal is selected from platinum, palladium, iridium, chromium, and mixtures thereof, preferably platinum.

In one embodiment, the solid support is selected from aluminium oxide, silicon dioxide, zirconium dioxide, titanium dioxide, magnesium oxide, calcium oxide, and mixtures thereof.

In another embodiment, the solid support comprises a mixed a magnesium-aluminium oxide, a mixed calcium-aluminium oxide, or a mixture thereof.

Additional active metal, which acts to enhance catalytic activity of this first catalyst, such as potassium, tin, lanthanum, indium, ytterbium, ytterbium, rhenium, and mixtures thereof, may be also present in the first catalyst, preferably tin, indium, and a mixture thereof.

In one embodiment, the first catalyst contains 0.01 to 25 wt % of the dehydrogenation active metal, preferably 0.05 to 20 wt % of the dehydrogenation active metal, more preferably 0.1 to 5 wt % of the dehydrogenation active metal, based on the total weight of the first catalyst.

In one embodiment, platinum is the dehydrogenation active metal, Al2O3 is the solid support and tin and/or potassium is the additional active metal in the first catalyst.

In another embodiment, platinum is the dehydrogenation active metal, SiO2 and ZrO2 are the solid support and yttrium and/or ytterbium is the additional active metal in the first catalyst.

In a further embodiment, platinum is the dehydrogenation active metal, a mixed magnesium-aluminium oxide and/or a mixed calcium-aluminium oxide is the solid support, and indium and/or tin is the additional active metal in the first catalyst.

In one embodiment, the mixed magnesium-aluminium oxide and the mixed calcium-aluminium oxide in the first catalyst are derived from a magnesium-aluminium or calcium-aluminium layered double hydroxide, which can be preferably obtained by subjecting a magnesium-aluminium or calcium-aluminium layered double hydroxide to a temperature in the range of 600-700° C., more preferably 600-650° C., for more 2 hours, more preferably 3 to 10 hours.

Preferably, the combined amount of the dehydrogenation active metal, the solid support, and the additional active metal present in the first catalyst is at least 90%, more preferably at least 95%, by weight of the first catalyst. In a particular embodiment, the first catalyst consists of the dehydrogenation active metal, the solid support, and optionally the additional active metal. In one embodiment, the transition metal of the third catalyst is selected from molybdenum, tungsten, rhenium, and mixtures thereof.

The transition metal is preferably tungsten, more preferably in the form of tungsten oxide.

In one embodiment, the inorganic support is selected from aluminium oxide, silicon dioxide, zirconium dioxide, titanium dioxide, zeolite, and mixtures thereof, preferably silicon dioxide or a mixture of silicon dioxide and zeolite.

In one embodiment, the third catalyst comprises tungsten on an inorganic support comprising a mix of silicon dioxide and zeolite.

Preferably, the zeolite is selected from ZSM-5, X-zeolite, Y-zeolite, beta-zeolite, MCM-22, ferrierite, and mixtures thereof, more preferably Y-zeolite.

In another preferred embodiment, the third catalyst e comprises a mixed metal oxide, more preferably a mixed magnesium-aluminium oxide, a mixed calcium-aluminium oxide, or a mixture thereof, wherein the mixed metal oxide is preferably physically mixed with the transition metal on the inorganic support.

In a particularly preferred embodiment, the third catalyst contains tungsten oxide on an inorganic support comprising a mixture of silicon dioxide and Y-zeolite physically mixed with a mixed magnesium-aluminium oxide.

Even more preferably is the mixed magnesium-aluminium oxide derived from a magnesium-aluminium layered double hydroxide precursor.

In one embodiment, the third catalyst contains 1 to 15 wt % of the transition metal, even more preferably 5 to 10 wt % of the transition metal, based on the total weight of the d catalyst.

In one embodiment, the third catalyst further comprises a doping agent selected from zinc, gallium, indium, lanthanum, and thereof. Preferably, the doping agent is supported on the inorganic support.

Preferably, the doping agent is present in the third catalyst in an amount of 0.1-10 wt %, more preferably in an amount of 1-5 wt %, based on the total weight of the third catalyst.

Preferably, the combined amount of the transition metal, the inorganic support, the mixed metal oxide, and the optional doping agent present in the third catalyst is at least 90%, more preferably at least 95%, by weight of the third catalyst. In a particular embodiment, the third catalyst consists of the transition metal, the inorganic support, the mixed metal oxide, and optionally the doping agent. The first catalyst is preferably prepared by supporting all element precursors of the dehydrogenation active metal and the optional additional active metal on the solid support followed by a suitable heat treatment.

Similarly, the third catalyst is preferably prepared by supporting on the inorganic support all element precursors of the transition metal and the optional doping agent followed by a suitable heat treatment.

Element precursors are starting compounds containing the desired elements which can be converted to the desired form of the elements in the final hydrocarbon conversion catalyst by the suitable heat treatment. For example, the element precursors may include oxides, halides, alkoxides, nitrates, carbonates, formats, oxylates, amines, or hydroxides of the elements.

More preferably, the first catalyst is prepared by impregnating, preferably simultaneously (co-impregnation), the element precursors of the dehydrogenation active metal and the optional additional active metal, which are provided in solution form, on the solid support followed by calcination. The calcination is preferably carried out in oxidizing atmosphere, at a temperature in the range of 300-800° C. for 1-24 hours, even more preferably 400-600° C. for 2-10 hours.

Also more preferably, the third catalyst is prepared by impregnating, preferably sequentially, the element precursors of the transition metal and the optional doping agent, which are provided in solution form, on the inorganic support followed by calcination. The calcination is preferably carried out in oxidizing atmosphere, at a temperature in the range of 300-800° C. for 1-24 hours, even more preferably 400-600° C. for 2-10 hours.

The first, second, and third catalysts can be in a powder form in one embodiment. In another embodiment, the first, second, and third catalysts can be also formed into a shape that is more suitable for industrial utilization, for example, pellet, tablet, date, or sphere.

In shaping of the first, second, and third catalysts, a binding material can be added to facilitate formation of powder into the desired shape. Any binding material known in the art may be used.

The object is further achieved by a process comprising contacting a hydrocarbon feed stream comprising a saturated hydrocarbon compound with the catalyst system according to the present invention.

In one embodiment, the hydrocarbon feed stream is passed through the catalyst system by contacting with the at least one layer of the first catalyst first, the at least one layer of the second catalyst second, and the at least one layer of the third catalyst third.

In one embodiment, the hydrocarbon feed stream comprises at least one paraffin having 2 to 5 carbon atoms, preferably selected from propane, n-butane, and a mixture thereof. In another embodiment, the hydrocarbon feed stream comprises a paraffin selected from ethane, propane, butane, and mixtures thereof, preferably propane, butane, and a mixture thereof, even more preferably, the hydrocarbon feed stream is propane.

The process according to the present invention can be operated in a wide range of operating conditions. However, some specific ranges of operating conditions can result in high olefins production selectivity.

In one embodiment, the process is carried out at a temp in the temperature of 200-800° C., preferably 350-700° C., even more preferably 450-650° C.

In another embodiment, the process is carried out at a pressure in the range of 0.01 to 10 bar gauge, preferably 0.05 to 5 bar gauge.

The contact time needed to obtain a desirable yield of olefins products depends upon several factors, such as operating temperature, operating pressure, and catalyst activity. In one embodiment, the process is carried out at a weight hourly space velocity (WHSV) in the range of 0.01 to 20 $hr^{-1}$, preferably 0.05 to 5 $hr^{-1}$.

Prior to contacting with the hydrocarbon feed stream, the catalyst system may optionally be pretreated. The pretreatment condition may include contacting the catalyst system with an inert gas, an oxidizing gas, a reducing gas, or mixtures thereof, at an elevated temperature, preferably 250° C. to 850° C., more preferably 400° C. to 750° C., even more preferably 500° C. to 700° C. In one preferred embodiment, the pretreatment condition includes contacting the catalyst with a reducing gas, more preferably hydrogen, at a temperature in the range of 500-700° C. for approximately 0.5 to 8 hours.

After contact with the hydrocarbon feed stream at the operating condition, some poisonous substances, heavy hydrocarbons, and coke may deposit on the surface of the catalyst system.

This normally affects activity of the catalyst mixture to gradually drop over time. A suitable regeneration can be performed on the used catalyst system to recover at least some of its activity.

In an embodiment, the hydrocarbon conversion process comprises a regeneration step wherein the regeneration step includes contacting the catalyst system with an oxidizing agent at a high temperature. The regeneration step should be carefully controlled to avoid overheating and destroying structure of the catalyst. In an embodiment, the regeneration step is carried out at a temperature in the range of 200° C. to 700° C., preferably 300° C. to 600° C. Other known regeneration techniques can be employed without limitation.

As can be taken from the above detailed description of the invention, in one embodiment, the first catalyst, the second catalyst and the third catalyst are different from each other.

A variety of the catalyst systems according to the invention have been prepared and tested according to the above disclosure. It was surprisingly found by the inventors that the hydrocarbon conversion process utilizing the catalyst system according to the present invention featured a satisfying level of paraffin conversion, olefins selectivity with good stability of the catalyst system.

EXPERIMENTAL RESULTS

Example 1 (Comparative)

Catalyst A was prepared by calcining a Mg—Al—CO3 layered double hydroxide in air at 620° C. for 8 hours to obtain a mixed magnesium-aluminium oxide support, then impregnated a solution of chloroplatinic acid and a solution of indium nitrate hydrate on the support. The obtained mixture was then dried at 110° C. and calcined at 620° C. The resulted Catalyst A contain 0.3 wt % Pt, 0.6 wt % In, on Mg—Al oxide support.

Catalyst B containing 7 wt % W, 4 wt % Y-zeolite, 10 wt % Mg—Al oxide, and balancing SiO2 was prepared by impregnating a solution of ammonium metaungstate hydrate, then dried at 110° C. for 3 hours. Then the resulted material was then mixed with Mg—Al—CO3 layered double hydroxide followed by calcination under air at 550° C. for 2 hours.

4 grams of the Catalyst was loaded into a ¾ inches stainless steel reactor, followed by 1.5 grams of the Catalyst A. The resulted catalyst bed was pretreated under hydrogen gas at 580° C. for 30 minutes. Then the catalyst bed was left to cool down to 570° C. before propane was fed through the catalyst bed, contacting with the Catalyst A first, at WHSV approximately 0.5 $hr^{-1}$.

Effluent from the reactor was sent to a Gas Chromatography equipment to measure product distribution. Result of this test is shown in Table 1.

Example 2

Catalyst A and Catalyst B were prepared using the method described in Example 1.

4 grams of the Catalyst B was loaded into a ¾ inches stainless steel reactor, followed by 1 gram of calcium oxide, and followed by 1.5 grams of the Catalyst A.

The resulted catalyst bed was subjected to pretreatment and reaction test condition as described in Example 1. Result of this test is shown in Table 1.

Example 3

Catalyst A and Catalyst B were prepared using the method described in Example 1.

4 grams of the Catalyst B was loaded into a ¾ inches stainless steel reactor, followed by 1 gram of magnesium oxide, and followed by 1.5 grams of the Catalyst A.

The resulted catalyst bed was subjected to pretreatment and reaction test condition as described in Example 1. Result of this test is shown in Table 1.

Example 4

Catalyst C was prepared by calcining a Mg—Al—CO3 layered double hydroxide in air at 620° C. for 8 hours to obtain a mixed magnesium-aluminium oxide support, then impregnated a solution of chloroplatinic acid and a solution of tin chloride hydrate on the support. The obtained mixture was then dried at 110° C. and calcined at 620° C. The resulted Catalyst C contains 0.3 wt % Pt, 0.6 wt % Sn, on Mg—Al oxide support.

Catalyst B was prepared as described in Example 1.

4 grams of the Catalyst B was loaded into a ¾ inches s less steel reactor, followed by 1 gram of calcium oxide, and followed by 1.5 grams of the Catalyst C.

The resulted catalyst bed was subjected to pretreatment and reaction test condition as described in Example 1. Result of this test is shown in Table 1.

TABLE 1

| Catalyst System | C3H8 Conversion (wt %) | Selectivity (% wt) | | | | | | | |
|---|---|---|---|---|---|---|---|---|---|
| | | Total Olefins | CH4 | C2H4 | C2H6 | C3H6 | C4H8 | C4H10 | C5+ |
| Example 1 | 30.06 | 84.29 | 5.05 | 19.47 | 8.84 | 37.21 | 17.85 | 1.81 | 9.64 |
| Example 2 | 24.01 | 90.44 | 4.66 | 20.65 | 4.20 | 42.24 | 18.17 | 0.69 | 9.39 |
| Example 3 | 31.96 | 87.14 | 4.95 | 20.24 | 6.85 | 38.24 | 17.32 | 1.05 | 11.35 |
| Example 4 | 34.44 | 88.28 | 4.58 | 19.61 | 6.07 | 40.29 | 18.53 | 1.07 | 9.85 |

Example 6 (Comparative)

Catalyst A and Catalyst B were prepared using the method described in Example 1.

4 grams of the Catalyst B was loaded into a ¾ inches stainless steel reactor, followed by 1.5 grams of the Catalyst A.

The resulted catalyst bed was subjected to pretreatment and reaction test condition as described in Example 1, but at WHSV of approximately 0.2 $hr^{-1}$. Result of this test is shown in Table 2.

Example 7

Catalyst A and Catalyst B were prepared using the method described in Example 1.

0.7 grams of the Catalyst B was loaded into a ¾ inches stainless steel reactor, followed by 1 gram of magnesium oxide, followed by 4 grams of the Catalyst A, followed by 1 gram of magnesium oxide, and followed by 1.5 grams of the Catalyst A.

The resulted catalyst bed was subjected to pretreatment and reaction test condition as described in Example 6. Result of this test is shown in Table 2.

TABLE 2

| Example | C3H8 Conversion (% wt) | Selectivity (% wt) | | | | | |
|---|---|---|---|---|---|---|---|
| | | Total Olefins | CH4 | C2H4 | C2H6 | C3H6 | C4H8 |
| Example 6 | 29.9 | 60.4 | 11.0 | 16.6 | 15.9 | 30.1 | 13.7 |
| Example 7 | 28.3 | 75.1 | 3.1 | 12.8 | 9.9 | 43.1 | 19.2 |

The features disclosed in the foregoing description and the claims may, both separately and in any combination thereof, be material for realizing the invention in diverse forms thereof.

The invention claimed is:

1. A catalyst system comprising:
    (a) at least one layer of a first catalyst comprising a dehydrogenation active metal selected from the group consisting of platinum, palladium, iridium, chromium, and mixtures thereof on a solid support;
    (b) at least one layer of a second catalyst comprising magnesium oxide, calcium oxide, or a mixture thereof; and
    (c) at least one layer of a third catalyst comprising a transition metal on an inorganic support;
    wherein the at least one layer of a second catalyst is sandwiched between the at least one layer of a first catalyst and the at least one layer of a third catalyst.

2. The catalyst system according to claim 1, wherein the solid support is selected from the group consisting of aluminum oxide, silicon dioxide, zirconium dioxide, titanium dioxide, magnesium oxide, calcium oxide, and mixtures thereof.

3. The catalyst system according to claim 1, wherein the first catalyst further comprises an additional active metal selected from the group consisting of potassium, tin, lanthanum, indium, yttrium, ytterbium, rhenium, and mixtures thereof.

4. The catalyst system according to claim 1, wherein the transition metal is selected from the group consisting of molybdenum, rhenium, tungsten, and mixtures thereof.

5. The catalyst system according to claim 1, wherein the inorganic support is selected from the group consisting of aluminum oxide, silicon dioxide, zirconium dioxide, titanium dioxide, zeolite, and mixtures thereof.

6. A process comprising contacting a hydrocarbon feed stream with the catalyst system according to claim 1.

7. The process according to claim 6, wherein the hydrocarbon feed stream is passed through the catalyst system by contacting with the at least one layer of the first catalyst first, the at least one layer of the second catalyst second, and the at least one layer of the third catalyst third.

8. The process according to claim 6, wherein the hydrocarbon feed stream comprises a paraffin selected from the group consisting of ethane, propane, butane, pentane, and mixtures thereof.

9. The process according to claim 6, wherein the process is carried out at a temperature in the range of 200-800° C.

10. The process according to claim 6, wherein the catalyst system is pretreated by contacting the catalyst system with an inert gas, an oxidizing gas, a reducing gas, or mixtures thereof at a temperature in the range of 250-850° C. prior to contacting with the hydrocarbon feed stream.

11. A catalyst system comprising:
(a) at least one layer of a first catalyst comprising a dehydrogenation active metal selected from the group consisting of platinum, palladium, iridium, chromium, and mixtures thereof on a solid support;
(b) at least one layer of a second catalyst comprising magnesium oxide, calcium oxide, or a mixture thereof; and
(c) at least one layer of a third catalyst comprising a transition metal on an inorganic support;
wherein the at least one layer of a second catalyst is sandwiched between the at least one layer of a first catalyst and the at least one layer of a third catalyst, and
wherein a weight ratio between the at least one layer of a first catalyst to the at least one layer of a third catalyst is in the range of 1:10 to 10:1.

12. The catalyst system of claim 11, wherein the first catalyst further comprises an additional active metal selected from the group consisting of potassium, tin, lanthanum, indium, yttrium, ytterbium, rhenium, and mixtures thereof.

13. The catalyst system of claim 11, wherein the transition metal is selected from the group consisting of molybdenum, rhenium, tungsten, and mixtures thereof.

14. A catalyst system comprising:
(a) at least one layer of a first catalyst comprising a dehydrogenation active metal selected from the group consisting of platinum, palladium, iridium, chromium, and mixtures thereof on a solid support;
(b) at least one layer of a second catalyst comprising magnesium oxide, calcium oxide, or a mixture thereof; and
(c) at least one layer of a third catalyst comprising a transition metal on an inorganic support;
wherein the at least one layer of a second catalyst is sandwiched between the at least one layer of a first catalyst and the at least one layer of a third catalyst, and
wherein the first catalyst contains 0.01 to 25 wt % of the dehydrogenation active metal.

15. The catalyst system of claim 14, wherein the first catalyst further comprises an additional active metal selected from the group consisting of potassium, tin, lanthanum, indium, yttrium, ytterbium, rhenium, and mixtures thereof.

16. The catalyst system of claim 14, wherein the transition metal is selected from the group consisting of molybdenum, rhenium, tungsten, and mixtures thereof.

17. A catalyst system comprising:
(a) at least one layer of a first catalyst comprising a dehydrogenation active metal selected from the group consisting of platinum, palladium, iridium, chromium, and mixtures thereof on a solid support;
(b) at least one layer of a second catalyst comprising magnesium oxide, calcium oxide, or a mixture thereof; and
(c) at least one layer of a third catalyst comprising a transition metal on an inorganic support;
wherein the at least one layer of a second catalyst is sandwiched between the at least one layer of a first catalyst and the at least one layer of a third catalyst, and
wherein the third catalyst further comprises a mixed magnesium-aluminum oxide, a mixed calcium-aluminum oxide, or a mixture thereof.

18. The catalyst system of claim 17, wherein the first catalyst further comprises an additional active metal selected from the group consisting of potassium, tin, lanthanum, indium, yttrium, ytterbium, rhenium, and mixtures thereof.

19. The catalyst system of claim 17, wherein the transition metal is selected from the group consisting of molybdenum, rhenium, tungsten, and mixtures thereof.

* * * * *